US010639355B2

(12) United States Patent
Ueda

(10) Patent No.: US 10,639,355 B2
(45) Date of Patent: May 5, 2020

(54) METHOD OF MAKING CONDITIONED MEDIUM FROM IMMORTALIZED DENTAL PULP STEM CELLS

(71) Applicant: QUARRYMEN & Co. Inc., Tokyo (JP)

(72) Inventor: Minoru Ueda, Tokyo (JP)

(73) Assignee: QUARRYMEN & Co. Inc., Tokyo (JP)

(*) Notice: Subject to any disclaimer, the term of this patent is extended or adjusted under 35 U.S.C. 154(b) by 0 days.

(21) Appl. No.: 15/113,646

(22) PCT Filed: Jan. 23, 2015

(86) PCT No.: PCT/JP2015/051887
§ 371 (c)(1),
(2) Date: Jul. 22, 2016

(87) PCT Pub. No.: WO2015/111712
PCT Pub. Date: Jul. 30, 2015

(65) Prior Publication Data
US 2017/0007677 A1 Jan. 12, 2017

(30) Foreign Application Priority Data
Jan. 24, 2014 (JP) ................. 2014-011729

(51) Int. Cl.
C12N 15/00 (2006.01)
A61K 38/30 (2006.01)
C12N 5/074 (2010.01)
A61K 35/12 (2015.01)
A61K 38/18 (2006.01)
A61K 38/19 (2006.01)
C12N 5/0775 (2010.01)
A61K 35/32 (2015.01)

(52) U.S. Cl.
CPC ............ A61K 38/30 (2013.01); A61K 35/12 (2013.01); A61K 38/1841 (2013.01); A61K 38/1866 (2013.01); A61K 38/195 (2013.01); C12N 5/0664 (2013.01); C12N 5/0696 (2013.01); A61K 35/32 (2013.01); C12N 2500/02 (2013.01); C12N 2500/90 (2013.01); C12N 2500/99 (2013.01); C12N 2501/105 (2013.01); C12N 2501/15 (2013.01); C12N 2501/165 (2013.01); C12N 2501/21 (2013.01); C12N 2501/60 (2013.01); C12N 2501/998 (2013.01); C12N 2506/1361 (2013.01); C12N 2510/04 (2013.01)

(58) Field of Classification Search
CPC ....................................... C12N 15/00
USPC ................................. 435/325, 455
See application file for complete search history.

(56) References Cited

U.S. PATENT DOCUMENTS 9,034,335 B2 * 5/2015 Herrera Sanchez ... A61K 35/28
424/184.1

FOREIGN PATENT DOCUMENTS

| EP | 2554175 A1 | 2/2013 |
| EP | 2832851 A1 | 2/2015 |
| JP | 2004000497 | * 1/2004 |
| JP | 2011-529329 | * 1/2010 |
| JP | 2011-529329 A | 12/2011 |
| JP | 2013-018756 | * 1/2013 |
| JP | 2013-018756 A | 1/2013 |
| JP | WO 2013/147082 | * 10/2013 |
| WO | WO-2010/013845 A1 | 2/2010 |
| WO | WO 2011/070001 | * 6/2011 |
| WO | WO-2011/118795 A1 | 9/2011 |
| WO | WO-2013/147082 A1 | 10/2013 |

OTHER PUBLICATIONS

Mita (J. Neurosci. Res., Jun. 2015, vol. 93, No. 6, p. 973-983).*
Song (J. Neurosci. Res., Jun. 2015, vol. 93, No. 6, p. 973-983).*
Nakagawa (Nat Biotechnol, Jan. 2008, vol. 26: 101-106; published online Nov. 11, 2007).*
Tamaoki (J. Dental Res., 2010, vol. 89, No. 8, p. 774-778).*
Egbuniwe (Cell Cycle, 2011, vol. 10, No. 22, p. 3912-3919).*
Translation for WO 2013/147082, 2017.*
Translation of Hasegawa (Japanese J. Pediatric Dentistry, 2012, vol. 50, No. 1, p. 7-14).*
Maqsood (Cell Biol. International, Oct. 2013, vol. 37, No. 10, p. 1038-1045).*
Tsai (J. Biomed. Sci., 2010, vol. 17, No. 64, p. 1-13).*
Translation of JP 2011-529329.*
Iida (Archives of Oral Biol., 2010, vol. 55, p. 648-654).*
Bronckaers (PLoS One, Aug. 2013, vol. 8, No. 8, e71104).*
Hendrix (Nature Reviews Cancer Apr. 2007, vol. 7, p. 246-255).*
Postovit (PNAS, Mar. 18, 2008, vol. 15, No. 11, p. 4329-4334).*

(Continued)

Primary Examiner — Michael C Wilson
(74) Attorney, Agent, or Firm — Locke Lord LLP

(57) ABSTRACT

The invention provides a novel anticancer therapeutic having a high effect against solid cancers, lacking the side effects of chemotherapeutics, and being unlikely to cause resistance. Provided is a pharmaceutical composition for cancer treatment prepared by a method having: a stem cell production step for making immortalized stem cells by introducing four types of genes into deciduous tooth dental pulp stem cells obtained from the dental pulp of mammals; and a condition medium preparation step for culturing the immortalized stem cells for a predetermined length of time in serum-free medium at 23-27° C. under conditions of low oxygen concentration at an oxygen concentration of from 0.5% to less than 20%, the pharmaceutical composition containing 1.5 times or more of insulin-like growth factor (IGF-1) and vascular endothelial growth factor (VEGF) than is contained in condition medium prepared when culturing at an oxygen concentration of 20% and otherwise identical conditions.

4 Claims, 9 Drawing Sheets
(5 of 9 Drawing Sheet(s) Filed in Color)

(56) References Cited

OTHER PUBLICATIONS

He (Stem Cell Research, 2016, vol. 7, No. 95, p. 1-13).*
Lee (Cancers, 2011, vol. 3, p. 3856-3893).*
Yue Wang, et al., "Hypoxia Promotes Dopaminergic Differentiation of Mesenchymal Stem Cells and Shows Benefits for Transplantation in a Rat Model of Parkinson's Disease," PLOS One, Jan. 2013, vol. 8, Issue 1, e54296 (12 pages).
M. Celeste Simon et al., "The role of oxygen availability in embryonic development and stem cell function," Nature Reviews/Molecular Cell Biology, Apr. 2008, vol. 9, pp. 285-296.
Tomokazu Hasegawa, "Investigation of New Strategy for Periodontal Tissue Regeneration Using with Human Immortalized Periodontal Ligament Cell Line Derived from Deciduous Teeth," Japanese Journal of Pediatric Dentistry, 2012, vol. 50 (1), pp. 7-14.
International Search Report dated Apr. 28, 2015, issued for PCT/JP2015/051887.
Andreza M.F. Aranha et al., "Hypoxia Enhances the Angiogenic Potential of Human Dental Pulp Cells", Journal of Endodontics, vol. 36, No. 10, Oct. 2010, pp. 1633-1637. (cited in the Sep. 8, 2017 EP Search Report).
Xiang Li et al., "Effects of hypoxia on proliferation and differentiation of myoblasts", Medical Hypotheses, vol. 69, No. 3, 2007, pp. 629-636. (cited in the Sep. 8, 2017 EP Search Report).
Ying Wang et al., "The hypoxia-inducible factor [alpha] pathway couples angiogenesis to osteogenesis during skeletal development", Journal of Clinical Investigation, vol. 117, No. 6, 2007, pp. 1616-1626. (cited in the Sep. 8, 2017 EP Search Report).
Extended European Search Report dated Sep. 8, 2017, issued for the European patent application No. 15740157.1.

* cited by examiner

Fig. 6
Example of complete healing
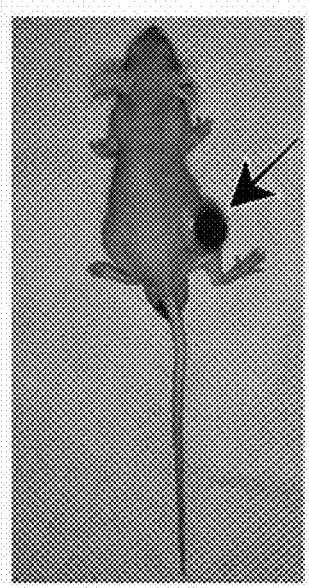 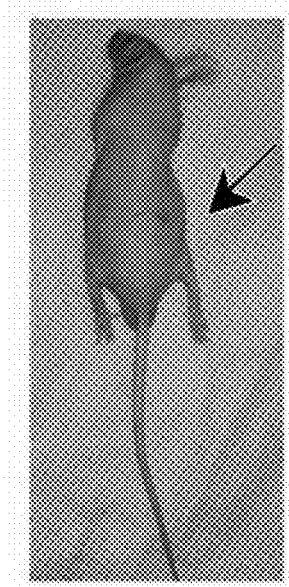
(A)  (B)

METHOD OF MAKING CONDITIONED MEDIUM FROM IMMORTALIZED DENTAL PULP STEM CELLS

TECHNICAL FIELD

The present invention relates to a pharmaceutical composition for cancer treatment and pharmaceutical preparation for cancer treatment thereof as active ingredient. Specifically, it relates to the pharmaceutical composition for cancer treatment by using a culture supernatant derived from mammal dental pulp stem cell and the pharmaceutical preparation comprising thereof as an active ingredient.

BACKGROUND ART

It is known that the hypoxic response in microenvironment in a body affects organ formation during development, proliferation of stem cell, and the like. Also, it is known that the effect of the hypoxic response relates to disease such as cancer and ischemic disorder.

Also, the hypoxic environment regulates expression of a variety of genes and controls cell response such as cell growth, differentiation, apoptosis and the like.

On the other hand, a variety of anticancer agents has been developed for cancer therapy. For example, there are mentioned as anticancer agent: cytarabine, fluorouracil, mercaptopurine and thioguanine as DNA synthesis inhibitors; vinblastine, vincristine and procarbazine as vinca alkaloids; mustine, cyclophosphamide and cisplatin of alkylating agent; actinomycin D, doxorubicin, mitomycin, mitramycin and bleomycin as antibiotics; and glucocorticoid, estrogen, anti-estrogen and androgen as steroid hormones and the like.

Cytarabine inhibits DNA polymerase, and fluorouracil inhibits thymidylate synthase to suppress pyrimidine synthesis. Mercaptopurine or thioguanine inhibits purine synthesis. Vinblastine or vincristine acts specifically to DNA in M phase, and destroy the spindle by binding to tubulin to stop mitosis of a cell. Procarbazine causes depolymerization of double strand DNA to inhibit DNA synthesis, and mustine, cyclophosphamide, cisplatin and the like cause covalent cross-link to inhibit DNA synthesis. Actinomycin D, doxorubicin, mitomycin, mitramycin and the like are intercalator, which are intercalating between a space formed by base pairs in double strand DNA, and block RNA synthesis. Also, bleomycin causes the breakage of the double strand DNA. Glucocorticoid, estrogen, anti-estrogen, androgen and the like inhibit the protein synthesis after RNA synthesis.

Other than that, a lot of anticancer drugs have been developed and used for treatment to exert a certain effect of treatment.

PRIOR ART

Patent Document

[Patent Document 1] WO 2011/118795

Non Patent Document

[Non Patent Document 1] Yue Wang, et al., PLOS ONE, January 2013, Vol. 8, Issue 1, e54296
[Non Patent Document 2] M. Celeste Simon and Brian Keith, Nature Reviews/Molecular Cell Biology, April 2008, Vol. 9, pp. 285-296

SUMMARY OF THE INVENTION

Problems to be Solved by the Invention

WO 2011/118795 discloses a composition for treatment of damaged portion of a target tissue, the composition containing culture supernatant obtained from a stem cell culture (hereinafter, it is referred to as, "prior art 1").

The prior art 1 is an excellent art from the view point that it found that culture supernatant of stem cell, which is cultured under the condition of standard oxygen concentration, may be used for treatment for damaged tissue by a variety of disease, and it leads to use it to develop an agent for damaged tissue caused by a cardiac disease or a cerebral vascular disease, both of which is one of the primary cause of death. Wherein, the culture supernatant contains at least two cytokine selected from the group consisting of vascular endothelial cell growth factor (VEGF), hepatocyte growth factor (HGF), platelet derived growth factor (PDGF) and insulin like growth factor (IGF-$\beta$), and the damaged tissue is for example, a central nervous tissue, a dermal tissue, a periodontal tissue, a bone tissue, a brain tissue and a retinal tissue. However, the prior art does not consider tumor (cancer), which is one of the primary cause of death.

As to cancer therapy, chemotherapy is usually conducted by using the anticancer agent as described above. However, the agent sometimes lose its effects in clinical, namely become drug-resistant. As the mechanism of the drug-resistance, there are mentioned, for example, caused by the vital response of the cancer patient such as inactivation of the anticancer drug or hypermetabolism thereof in liver, and biochemical changes at a cancer cellular level. Among them, it is considered that following matters are happened: the change of membrane transport mechanism of anticancer drug related to multidrug resistance, amplification of target enzymes or proteins, drug activation mechanism, reduced enzyme activity, for example, increase of DNA repair mechanism, enhanced inactivation mechanism of anticancer drug, and the like occur. Also, most of anticancer drugs have serious side effects, and it sometimes leads the cancer patient to die.

Therefore, there are strong needs about the method for cancer therapy having few side effects. Immunotherapy draw attention as the cancer therapy having few side effects. However, it has low tumor control capability so that it cannot consistently eliminate the tumor. Since the immunotherapy is utilizing lymphocyte or NK cell, which are main players of immunity, and have less inhibitory effect on solid tumor because they are primarily responsible for infectious disease.

Therefore, there is a strong social request to develop a novel agent for the cancer therapy which is highly effective on the solid tumor without side effect brought by chemotherapeutic drug, and is rarely gives resistance to the cancer cells.

Means for Solving the Problem

The inventors of the application conducted a research for biological abilities of dens deciduous stem cell (SHED) under such circumstances to find that the culture supernatant of SHED (hereinafter, it is sometimes referred to as "SHED-CM") controls functions of macrophage (hereinafter, it is sometimes referred to as, "M"), and complete the invention.

That is, the first aspect of the present invention is a pharmaceutical composition for cancer therapy prepared by a method comprising the steps of: manufacturing an immortalized stem cell by transfecting 4 gene into dens deciduous dental pulp stem cell derived from mammal dental pulp; and preparing a conditioned medium by culturing said immortalized stem cell in a serum free medium for predetermined period under the condition of hypoxic concentration of 0.5% or more but less than 20% of oxygen concentration between the temperature of 23 to 27° C.; wherein the conditioned medium comprises more than 1.5 times higher concentration of both insulin like growth factor 1 (IGF-1) and vascular endothelial cell growth factor (VEGF), compared to the conditioned medium prepared by culturing the cell on the same condition except the oxygen concentration is set to 20%.

Here, it is preferable that the predetermined period is 40 to 56 hours, and that the hypoxic concentration means that oxygen concentration is 5% or less. Also, it is preferable that hypoxic concentration means that oxygen concentration is 1% or less. It is preferable that said 4 gene is selected from the group consisting hTERT, bmi-1, E6, E7, Oct3/4, Sox2, Klf4, c-Myc, and p16INK4a.

It is preferable that the pharmaceutical composition for cancer treatment prepared by the above method further comprises at least five times higher concentration of transforming growth factor β (TGF-β1) compared to the conditioned medium prepared by culturing the stern cell under the same condition except the oxygen concentration is set to 20%. It is preferable that the pharmaceutical composition for cancer therapy further comprises at least three times higher concentration of stromal cell-derived factor (SDF-1).

Also, another aspect of the invention is the pharmaceutical preparation for cancer treatment that contains the condition medium obtained from the above method as active ingredient. It is preferable that the cancer is the solid tumor.

Advantageous Effect of the Invention

According to the present invention, the pharmaceutical composition, which comprises significantly higher concentration of IGF-1 and VEGF under hypoxic concentration and the predetermined culture conditions compared to that obtained by using culturing at 20% of oxygen concentration, is obtained.

And then, the population of macrophage accumulating around solid tumor is controlled by administration of the pharmaceutical composition to enable to control the growth of the cancer cells or kill them.

BRIEF DESCRIPTION OF DRAWINGS

The patent or application publication contains at least one drawing executed in color. Copies of this patent or patent application publication with color drawings will be provided by the Office upon request and payment of the necessary fee.

In FIG. 1, SHED-T shows the immortalized stem cell, and SHED-C shows non-immortalized stem cell.

FIGS. 2(A) and 2(B) are the graphs showing the relative cell number of SHED-C, which is described as "normal cell" in the figure, expressing STRO-1 at PD 20 and PD 30 respectively. FIGS. 2(C) and 2(D) are the graph showing the relative cell number of SHED-T, which is described as "immortalized stem cell" in the figure, expressing STRO-1 at PD 20 and PD 40 respectively.

FIGS. 3(A) to 3(F) shows the images of the inoculant recovered from each mouse eight weeks after the inoculation stained with hematoxylin and eosin.

The mass of newly generated bone = area of the newly generated bone / sight area×100

Figure 5:
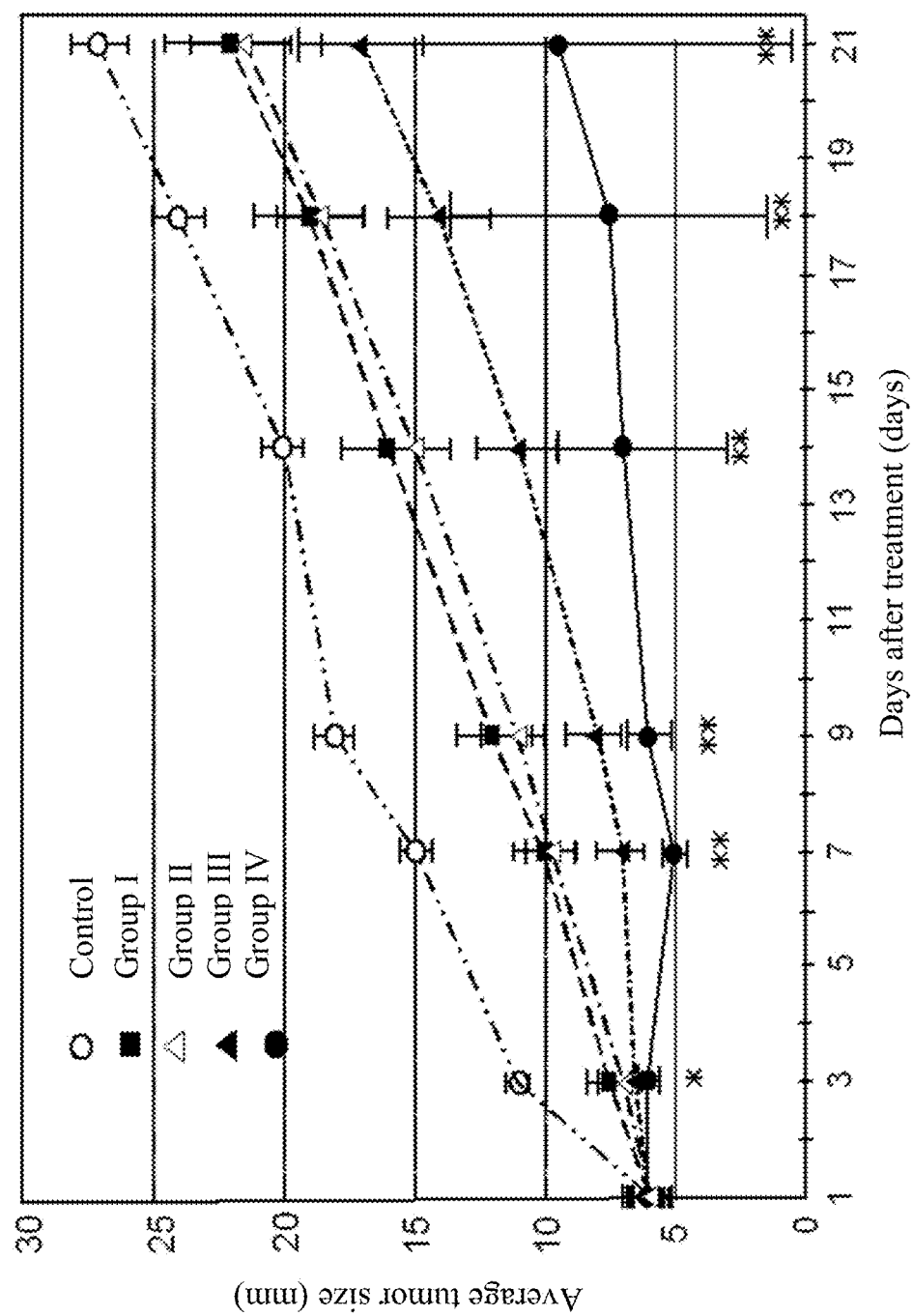

FIG. 5 shows the result of time course change of tumor volume after injecting SCCVII subcutaneously, when the culture supernatants of SHED cultured under different conditions are administered. In the figure, * shows p <0.05, ** shows p <0.001 obtained from ANOVA analysis.

FIGS. 6(A) and 6(B) show photographs illustrating that the culture supernatant obtained from SHED-T by culturing under different oxygen concentration inhibits the growth of mouse squamous cell cancer strain SCCVII inoculated under the skin on the back of 7 week-old mouse. FIGS. 6(A) and 6(B) show the tumor having the volume over 10 mm in diameter that regressed completely, respectively.

Figure 7:
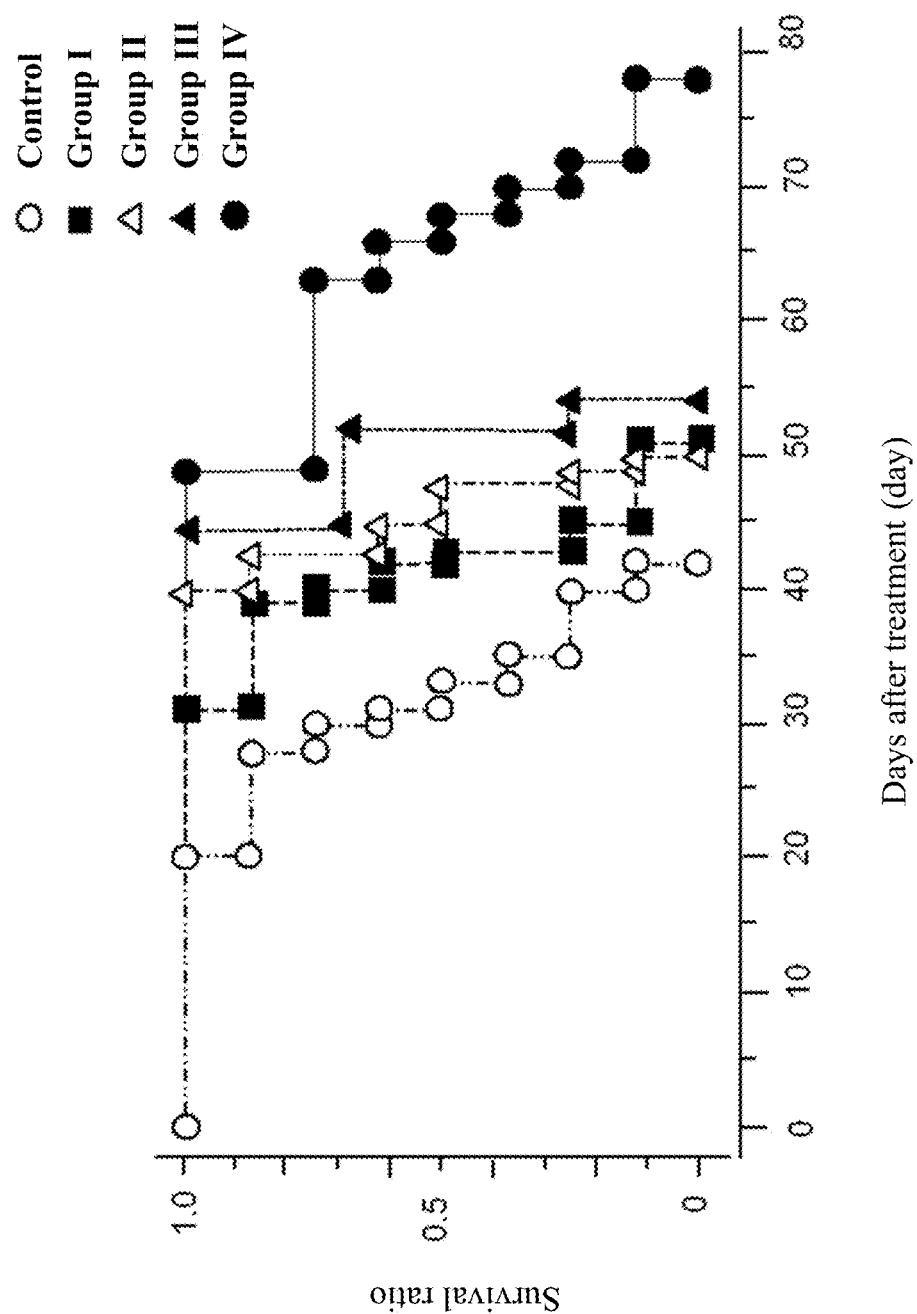

FIG. 7 shows survival ratio of each group of mouse injected SCCVII subcutaneously.

Figure 8:
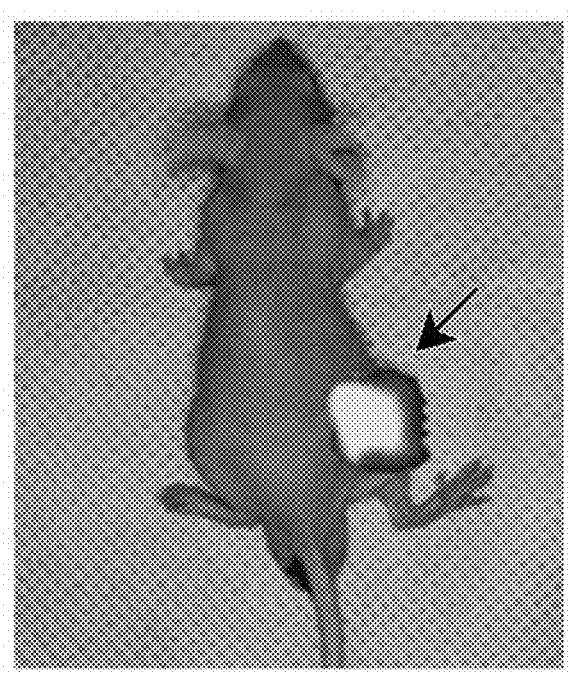

FIG. 8 is the in vivo image showing that $1 \times 10^7$ cells of macrophage labeled with IVIS (registered trade mark) XenoLight DiR (Summit Pharmaceutical International Co.) is injected to a tumor bearing mouse via tail vein.

Figure 9:
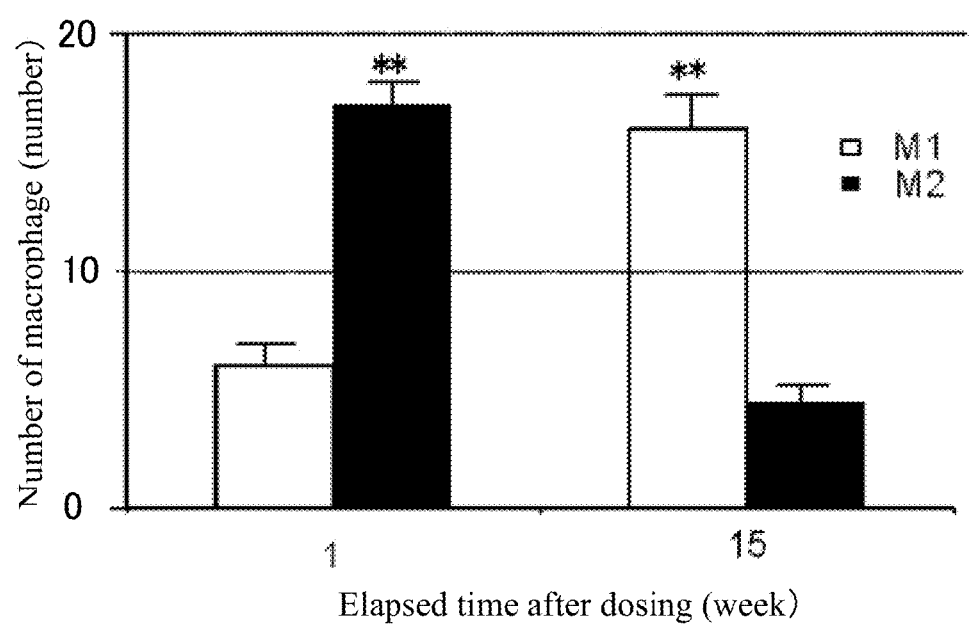

FIG. 9 shows a population change of intraperitoneal macrophage in the solid tumor bearing mouse by SCCVII.

FIGS. 10(A), 10(B), 10(C), and 10(D) show the result of the histological examination of hematoxylin and eosin stained solid tumor formed in mice after being inoculated with mouse squamous cell cancer strain SCCVII. FIGS. 10(A) and 10(C) show the result of the control group, while FIGS. 10(B) and 10(D) show the result of the treated group. FIGS. 10(A) and 10(B) are low magnification images, and FIGS. 10(C) and 10(D) are high magnification images.

MODE FOR CARRYING OUT THE INVENTION

The present invention is explained in detail in below.

In order to obtain the immortalized stem cell of the present invention, firstly, the stem cell is isolated from a mammal mesenchymal cell, early generated embryo, and somatic cells. As the mammal animal, it is preferable to be selected from the group consisting of human, swine, equine, and monkey, because the cells obtained from the mammal are genetically similar to the human cells and are not so dangerous for infectious disease.

In the present specification, the term, "mesenchymal cell", is defined as the cells having differentiation ability into the cells belonging to the mesenchymal such as osteoblast, adipocyte, muscle cell, cartilage cell, and the like. As the specific mesenchymal cell, the dental pulp cell, hone marrow cell, umbilical cell and adipocyte of the above-mentioned animals are mentioned. Also, the term, "early-generated embryo", is defined as the embryo in the early stage by the blastocyst, namely, it is in the progressed stage than the fertilized egg, and necessary for establishing ES cell. The term, "somatic cell", is defined as the general term of the cell except a germ cell among those which compose of a living body.

Furthermore, the term, "dental pulp cell", is one of the stem cells included in the nerve of the teeth, which has the regeneration ability. Since it is protected by hard material, teeth, which does not permeate UV light or radioactive ray, the genes in them is not easily damaged. The term, "bone marrow cell", is defined as the general term of the cells obtained from bone-marrow aspirate, and it includes a leukocyte series cell such as a myeloblast cell, an erythroblast series cell, a megakaryocyte cell, and plasma cells and the like.

In the present specification, the term, "umbilical cell", is that exists in the umbilical cord, which binds the embryo and a placenta. It is included in the umbilical cord, and also includes umbilical blood having abundant hematopoietic stem cells.

As the genes introduced into the stem cells as described above, hTERT, bmi-1, E6, E7, Oct3/4, Sox2, Klf4, c-Myc, p16INK4a, and the like are mentioned. hTERT is a gene for telomere repair enzyme; bmi-1 is the gene of Bmi-1, which is one of proteins composing of polycomb group complex. Here, Bmi-1 is necessary for maintaining the hematopoietic stem cells, which has the effect to increase the stem cell by activity enhancement.

Both E6 and E7 are early genes of either HPV-16 or HPV-18. Also, Oct3/4 is the gene that cooperates with Sox2 to activate the transcription of the target gene. Klf4 (Kruppel type transcription factor 4) regulates the genes relating to the cell division and the embryogenesis, and it relates to the gastrointestinal system cancer as the tumor suppressor.

Sox2 belongs to SRY-related HMG box gene family, and it is known as the gene that relates to the maintenance of undifferentiated functions (totipotency). c-Myc is a cancer promoting gene, and it promotes both of survival and death of the cell in the c-Myc-induced tumor. p16INK4a is the gene which plays an important role to control the cell cycle of the tumor cell.

The of the immortalized stem cell manufacturing is explained as an example by using the dental pulp obtained from the human exfoliated dens deciduous teeth as follow.

Firstly, the exfoliated dens deciduous are disinfected by using a disinfection agent, for example, chlorhexidine, Isodine, and the like. After that, a crown of the tooth is divided, and dental pulp is collected by using dental reamer.

Obtained dental pulp tissue is suspended in the basal media, for example, such as Dulbecco's modified eagle's MEM (Dulbecco's Modified Eagle's Medium, herein below, it is referred to as "CS") containing 5 to 15% (v/v) of calf serum (herein below, it is sometimes referred to as "DMEM"), and 50 to 150 U/mL of antibiotics. Then, they are treated by using 1 to 5 mg/mL of collagenase and 1 to 5 mg/mL of dispase at 37° C. for 0.5 to 2 hours.

As the basal media, other than DMEM, Iscove's Modifed Dulbecco's Medium (IMDM) (GIBCO, etc.), Ham's F12 medium (HamF12) (SIGMA, GIBCO, etc.), RPMI1640 medium, and the like may be used. Also, a mixed media comprising at least two media may be used. As an example of the mixed medium, a medium including IMDM and HamF12 in equal amount (for example, it is commercially available as the product name: IMDM/HamF12 (GIBCO)) is mentioned.

As the components to be added to the media, for example, serum (fetal calf serum, it is referred to as "FCS"), human serum, sheep serum and other serum, serum replacement (Knockout serum replacement (KSR), etc.), bovine serum albumin (it is referred to as "BSA"), antibiotics such as penicillin, streptomycin and others, various vitamins, various minerals, and the like are mentioned.

The basal medium may be also used to culture for the selection of cells as mentioned below, and used to culture for the selected cells.

After enzyme treatment, centrifugation operation is performed for 3 to 10 minutes (3,000 to 7,000 rpm) to collect the dental pulp cell. Depending on the necessity, the cells are selected by using a cell strainer. The selected cells are, for example, resuspended in 3 to 6 mL of the basal medium to plate in a dish having 4 to 8 cm of diameter for adherent cell culture.

Subsequently, the medium, for example, DMEM containing 10% FCS is added, and then the cells are incubated in 5% $CO_2$ incubator at 37° C. for about 2 weeks. After removal of the medium, the cells are washed from 1 to several times with PBS and the like. Instead of the removal of the medium and wash of the cells, the adherent dental stem cells which formed colonies may be collected. The adherent dental stem cells are treated by using a solution including both of 0.025 to 0.1% trypsin and 0.3 to 1 mM EDTA for several minutes at 37° C. to be detached from the dish. Next, the detached cells are collected.

Subsequently, the selected adherent cells are cultured. For example, the stem cells obtained as mentioned above are plated to the dishes for the adherent cell culture, and then cultured under the conditions of 5% $CO_2$ and at 37° C. in the incubator.

For passage culture, the cells are collected by using trypsin and EDTA as mentioned above when the cells become sub-confluent or confluent with macroscopic observation. Then, the cells are plated again in the culture dish containing the culture medium.

Here, the term, "sub-confluent", means the situation that the cells adhere about 70% of the bottom area of the culture vessel. For example, the passage is performed 1 to 8 times, and selected cells are propagated up to the necessary cell number, for example, about $1 \times 10^7$ cells/mL. After culturing as described above, the cells are collected to store in liquid nitrogen. The cells collected from a variety of donor may be stored in the form of dental pulp stem cell bank.

Next, the 4 genes are introduced into the primary-cultured cells obtained from the primary culture of the stem cells to create gene-transduced cells. The genes transduced here are preferably 4 types selected from the group consisting of hTERT, bmi-1, E6, E7, Oct3/4, Sox2, Klf4, c-Myc, and p16INK4a. By introducing hTERT, bmi-1, E6, and E7, the immortalized cells having higher population doubling time may be obtained. Here, hTERT is the gene for human telomerase reverse transcriptase; bmi-1 is the polycomb group gene relating to auto-reproduction or differentiation regulation of the stem cell. E6 and E7 are genes existing in an open reading frame coding early gene used to replicate human papilloma virus itself.

Such genes may be introduced as follows.

A plasmid for insertion of the target genes is prepared, and then it is inserted into a shuttle vector, for example, pShuttle2 to clone the genes. E. coli is transformed by using the shuttle vector to select kanamycin resistant transformant. Plasmid DNA of the selected kanamycin resistant transformant is purified to identify a recombinant by analyzing restriction sites.

Next, a restriction enzyme, for example, PI-Sce I and I-Cue I are used to cut out an expression cassette from the shuttle vector; then it is ligated into adenovirus vector, for example, Adeno-X viral DNA. Obtained ligation product is cleaved by using Swa I, and it is used to transform the *E. coli*.

From the obtained transformants, ampicillin resistant transformants were selected. The recombinant adenovirus DNA to which the genes are inserted is purified to identify the transformant by analyzing the restriction sites.

Next, the adenovirus is digested by using Pac I to transfect HEK 293 cells. The recombinant adenovirus is propagated, and then collected to measure their titers. According to a conventional method to purify the virus, it is used to infect the target cell, SHED.

Cell population infected with the virus is stained by using FITC according to the conventional method, and then STRO-1 positive cells are detected by using a flow cytometer. Here, STRO 1 is considered as one of markers for the mesenchymal stem cell having pluripotency in the bone marrow, and it becomes an index for cell immortalization.

According to the above-mentioned procedure, the immortalized stem cell derived from the dental pulp may be obtained.

Next, the obtained immortalized stem cell is cultured in the basal medium, for example, DMEM supplemented with 10% FBS under the condition of 5% $CO_2$ at 37° C. for 24 to 48 hours to obtain the culture supernatant. In order to collect the culture supernatant, for example, a Komagome type pipette and the like may be used. The collected culture supernatant may be used as an active ingredient for the pharmaceutical composition of the present invention as it is. Also, it may be used as the active ingredient after treatments such as condensation, replacement of the solvent, dialysis, lyophilization, dilution and others.

As described below, the culture supernatant of the immortalized stem cell obtained as mentioned above includes a variety of growth factors, and it shows many functions without highly purification. Namely, the pharmaceutical composition of the present invention to be used in many diseases may be produced in a convenient process. Therefore, it may be avoided to decrease bioactivities of the growth factors caused by the highly purification.

Note that the "culture supernatant of the immortalized cell" used in the present invention is defined as the culture supernatant including a variety of biological factors obtained by culturing the immortalized stem cell, and it is the solution that does not include any cells such as the immortalized stem cells and other cells. When the culture supernatant without serum is prepared, it is preferable to use serum-free medium in entire process from initial culture to the passage or at several passage prior to collect the cells.

The dental pulp stem cell selected and cultured by using the above-mentioned method is a cell obtained from the tissue and cell of the living body and has the same properties as the primary cultured cell. In general, the primary cultured cell has similar properties to those of the organ as the source, and it is important that their properties are close to the normal cell. However, it grows slower compared to the cell line, and sometimes it dedifferentiates during continuous culture. Therefore, it is difficult to maintain the cell keeping the properties.

However, the immortalized stem cell of the present invention has significantly higher expression ratio of STRO-1, which becomes the marker of anaplastic degree of the cell, compared to that of the dental pulp stem cell which is not the immortalized cell as of 20 or 40 times of population doubling time. It is preferable that the immortalized stem cell shows about 1.5 to 3 times as higher ratio, because the height of expression ratio of STRO-1 becomes the index that the cell shows the same properties as that of the primary cultured cell.

Also, the immortalized stem cell of the invention secretes at least two growth factors selected from the group consisting of insulin-like growth factor (IGF), vascular endothelial growth factor (VEGF), transforming growth factor-β(TGF-β), and hepatocyte growth factor (HGF) into the culture supernatant. Here, the term "growth factor" is a general term of polypeptide which promotes the cell division and causes the morphological change or cell hypertrophy. The growth factors are different depending on the kind of cell which produce them, and they are roughly classified into epidermal growth factor (EGF), fibroblast growth factor (FGF), nerve growth factor (NGF), tumor growth factor (TGF) and the like.

Furthermore, the receptors on the cell membrane of each cell have tyrosine kinase activity. When the growth factors bind them, tyrosine residues of the proteins are phosphorylated to cause the cell growth or proliferation. It is known that there are several examples that the growth factor becomes a mesoderm inducer in the ontogenesis. Also, it is known that there are several examples that the lymphokine, which modulates the immune system, becomes the mesoderm inducer in the ontogenesis. Such growth factors may be quantified by using the ELISA assay, microarray assay and the like.

IGF-1 is the polypeptide having highly similar sequence to insulin, and it causes reactions such as mitogenesis and the like in the culture cells as insulin does. It is also known that IGF-1 affects the nerve cell growth. Also, VEGF is a glycoprotein family involving to vascurogenesis, which newly forms blood vessels in the area without the blood vessels are not yet at period of embryogenesis, and to angiogenesis, which newly forms the blood vessels by branching and extending from already existed blood vessels. TGF-β also becomes a powerful growth inhibitor against a variety of the cells, tightly involves to the cell differentiation, migration and adhesion, and plays an important role in a broad region such as ontogenesis, tissue reconstruction, wound healing, inflammation and immunity, cancer invasion and metastasis, and the like. Furthermore, HGF has a variety of physiological activity involving the regeneration and protection of the tissue and the organ such as the promotion of the cell proliferation and cell motion, anti-apoptosis (cell death), morphogenetic induction, angiogenesis and others for the various cells other than hepatocyte.

Each stem cell as mentioned above is cultured, for example, in DMEM supplemented with 15% FCS at 37° C. in the predetermined term, thereby the protein as mentioned above was obtained in culture supernatant including the growth factors. Note that the culture supernatant of the stem cell includes about 70 types of proteins besides IGF-1, VEGF, TGF-β, and HGF.

15 mL of the culture supernatant obtained is poured into Amicon Ultra Centrifugal Filter Units-10K (Millipore Limited). Then, it is centrifuged with ×4,000 g for about 60 minutes to concentrate up to about 200 μL. Next, the same volume of sterilized PBS as the culture supernatant poured into the tube, and centrifuged again with ×4,000 g for about 60 minutes to replace the solvent to PBS. The obtained 200 μL of the solution is collected into the micro test tube to obtain the condensed stem cell culture supernatant.

Instead of the method by using the Amicon as described above, the concentration may be performed by using ethanol precipitation method. For example, 45 mL of 100% ethanol is added to 5 mL of the culture supernatant to mix them and then stood at −20° C. for 60 minutes. After that, it is centrifuged with ×15,000 g for 15 minutes at 4° C. to remove supernatant.

Next, for example, 10 mL of 90% ethanol is added to mix well, and then again centrifuged with ×15,000 g for 5 minutes at 4° C. After removing the supernatant, the obtained pellet may be dissolved, for example, in 500 μL of the sterilized water. After the dissolution, the entire volume is collected in the micro test tube, and the concentrated stem cell culture supernatant is obtained.

The culture supernatant obtained as mentioned above may be used as it is, and also be used after dilution appropriately with physiologically acceptable solvent such as phosphate buffered saline. Also, it may be used for pharmaceutical composition prepared at the time of use according to the conventional method.

The content of the growth factor in the culture sup included in the pharmaceutical preparation is preferably about 50 to 500 weight % against the total dry weight thereof.

As the dosage form of the pharmaceutical preparation, powder, liquid, gel, spray, percutaneous absorption system and the like are mentioned. For example, the pharmaceutical preparation may be prepared by adding additives such as a filler, an excipient, an acidity regulator and the like to pour into a small sized container such as a sterile glass ample, serum tube and the like. When using it, it is dissolved by using saline or sterile distilled water for injection, and then may be administrated via transnasal administration. Alternatively, it may be administrated by using a sheet of gauze infiltrated with the solution to adhere the affected area. When it is used for osteogenesis of the alveolar bone and other bones, collagen, β-TCP and the like may be used as a scaffolding member, which are immersed in the dissolved solution to be embedded.

The sub-population of macrophage in the body is controlled by administering the above obtained culture supernatant by a variety method such as intravenous administration, which leads to treat tumor treatment.

EXAMPLES

The present invention is described more specifically by using examples as below, however, it is not limited to the examples.

Example 1

Preparation of Immortalized Cell (1) Construction of Vector for Virus Introduction
(1-1) Reagent and the Like for Plasmid Extraction Kanamycin (Kan), ampicillin (Amp), LB liquid medium and LB agar medium, glycogen, agarose, sterilized water, ammonium acetate, sodium acetate, sodium dodecyl sulfate and RNase A were used. Both 50 mg/mL of kanamycin and ampicillin were prepared to store them as stock solutions at −20° C. Glycogen was prepared at the concentration of 20 mg/ml. 10 mg/ml of RNase A was prepared to store at −20° C. 10 M (saturated) ammonium acetate ($NH_4OAc$) and 3M sodium acetate (NaOAc; pH 5.2) were prepared.

(1-2) Restriction Enzyme and the Like

*E. coli* competent cell (Supercharge EZ10 Electro competent Cells, product code 636756), Swa I (the product code 1111A, Smi I is a comparable one), Xho I (the product code 1094A), T4 DNA Ligase (the product code 2011A), NucleoBond Xtra Midi (the product code 740410.10/.50/.100), NucleoSpin Plasmid (the product code 740588 10/50/250) were purchased from Takara Bio Inc. Pac I was purchased from New England Biolabs.

(1-3) Buffer and the Like

1× TE Buffer (10 mM Tris-HCL (pH 8.0) including 1mM EDTA), which is a mixture of saturated phenol:chloroform: isoamyl alcohol (25:24:1), hereinafter, it is referred to as "PCI solution"), was prepared. Ethanol was used either 100% or 70%. In order to purify pAdeno-X plasmid DNA used in a mini scale recombination, the following buffers 1 to 4 were prepared.

Buffer 1: 25 mM Tris-HCl including 10 mM EDTA and 50 mM glucose (pH 8.0) (after autoclave, stored at 4° C.)

Buffer 2: 0.2M NaOH including 1% of SDS (prepared immediately before the time of use, tightly sealed and stored at room temperature)

Buffer 3: 5 M KOAc (after autoclave, stored at 4° C.)

Buffer 4: 10 mM Tris-HCl (pH 8.0) including 1 mM EDTA and 20 μg/ml of RNase (RNase is added immediately before use, stored at −20° C.)

(2) Purification of Adenovirus and Reagents for β-gal Assay

HEK293 cell (ATCC #CRL1573) transformed by human type V adenovirus was used. HEK293 cell was cultured in a complete medium. The composition of the complete medium was DMEM (Dulbecco's Modified Eagle's Medium, the basal medium) supplemented with 100 unit/ml of sodium penicillin G, 100 μg/ml of streptomycin, 4 mM glutamine, and 10% FBS. Sodium penicillin G solution was prepared at the concentration of 10,000 units/ml, and streptomycin sulfate solution was prepared at that of 10,000 μg/ml. They were stored as the stock solutions.

In the culture, 60 mm plates, 100 mm plates, 6-well plate, T75 and T175 flasks were used.

Trypsin-EDTA (the product code CC-5012) was purchased from Takara Bio Inc. Phosphate buffered saline (PBS, without $Ca^{2+}$ and $Mg^{2+}$) and Dulbecco's phosphate buffered saline (DPBS, with $Ca^{2+}$ and $Mg^{2+}$) were prepared. Also, 0.33% neutral red stain solution, and 0.4% trypan blue stain solution were used.

In β-gal assay, X-Gal (5-bromo-4-chloro-3-indolyl-β-D-galactopyranoside (25 mg/ml)) in dimethylformamide (DMF) solution was stored at −20° C. in a light resistant container. Luminescent β-gal Detection Kit II (the product code 631712) was used.

(3) Preliminary Test
(3-1) Construction of Recombinant Adenovirus including lacZ (pAdeno-X-lacZ)

After thawing, HEK293 cells which removed DMSO from the solution were resuspended in 10 mL of the complete medium. Then whole amount was transferred onto the culture plate having a diameter of 100 mm. After HEK293 cells adhered to the plate, the culture medium was removed. Then, the cells were washed once with sterile PBS. After that, 1 ml trypsin-EDTA was added to treat them for about 2 minutes.

Next, 10 ml of the complete medium was added to stop the reaction of trypsin, and then the cells were mildly suspended. By using viable count, $10^5$ cells were transferred into the plate having 100 mm diameter including 10 mL medium to spread out evenly.

pShuttle2-lacZ (a positive control vector included in Adeno-X Expression System 1) and Adeno-X Viral DNA (PI-Sce I and I-Ceu I digested) included in the kit was used. According to a protocol attached in the kit, the recombinant adenovirus including lacZ was constructed. It was infected to the target cell, SHED, and the expression of β-garactosidase was assayed to confirm that the vector was constructed.

(3-2) Construction of the Recombinant pShuttle2 Plasmid

Prior to the construction of the recombinant pShuttle2 Vector (herein below, it is referred to as "rpShuttle2 Vector".), *E. coli* DH5α was transformed with pShuttle2 Vector and pShuttle2-lacZ Vector, included in the kit. Transformants were selected on LB agar plate including 50 μg/ml of kanamycin (herein below, it is referred to as "LB/Kan".). Bacterial cells obtained from a single colony were streaked on new LB/Kan to be incubated at 37° C. for overnight.

Next, hTERT, bmi-1, E6, and E7 were cloned into pShuttle2. A pShuttle2 vector was cleaved by using a restriction enzyme suitable for these genes.

Next, referring pShuttle2 Vector Information Packet (PT3416-5) attached to the kit, multi cloning site matching insert DNA was decided. The plasmid treated with the restriction enzyme was treated by using alkaline phosphatase to be purified.

According to the conventional method, target DNA fragments were prepared to be purified. The vector digested with the restriction enzyme and the gene fragments were ligated. By using the ligation product, DH5α cells (competent cell) were transformed. A portion of the competent cell was taken to be transformed by using a control vector, pShuttle2-lacZ Vector included in the kit to use as a positive control.

The mixture including transformed *E. coli* was plated on the LB/Kan agar plate to select kanamycin resistant (Kam) transformant (a colony). Five to 10 Kan resistant clones were selected, and they were plated in a small amount of the liquid medium to be amplified. After confirmation that these clones have rpShuttle2 Vector, they were incubated overnight. Then, by using a commercially available silica gel adsorption column, the constructed plasmid DNA was purified according to the conventional method.

The plasmid DNA was treated with the restriction enzyme to be subjected to 1% agarose gel electrophoresis; thereby the target recombinant plasmid was identified. By sequencing, the direction of the inserted fragment and inserted site were confirmed to identify the positive clone.

The recombinant pShuttle2 plasmid DNA (herein below, it is referred to as "rpShuttle2 plasmid DNA") was directly transfected into the target cell, and then it was subjected to western blot to check the target protein expression preliminary.

(3-3) Double Digestion of rpShuttle2 Plasmid DNA with PI-Sce I/I-Ceu I

From the rpShuttle2 plasmid DNA produced as mentioned above, an expression cassette of the inserted gene was taken out by using PI-Sce I and I-Ceu I. According to in vitro ligation method written in the protocol attached to the kit, the expression cassette taken out was integrated into Adeno-X Viral DNA. 30 μl of PI-Sce I/I-Ceu I double-digestion solution for the rpShuttle2 plasmid DNA was prepared. The reagents shown in the following table 1 were entered into 1.5 ml of the sterilized micro centrifuge tube and mixed.

TABLE 1

| Reagent and others | Tube 1 (μL) | Tube 2 (lacZ control)(μL) |
|---|---|---|
| sterilized water | 19.5 | 19.5 |
| 10× double-digention solution | 3.0 | 3.0 |
| rpShuttle2 plasmid DNA (500 ng/μl) | 2.0 | — |

TABLE 1-continued

| Reagent and others | Tube 1 (μL) | Tube 2 (lacZ control)(μL) |
|---|---|---|
| pShuttle2-lac Z plasmid (500 ng/μl) | — | 2.0 |
| PI-Sce I (1 unit/μl) | 2.0 | 2.0 |
| I-Ceu I (5 unit/μl) | 0.5 | 0.5 |
| 10× BSA | 3.0 | 3.0 |
| Total | 30.0 | 30.0 |

Next, after sufficiently mixing, the micro centrifuge tube was lightly centrifuged, and then incubated for 3 hours at 37° C.

The double digested reaction mixture (5 μl) was subjected to 1% agarose/EtBr gel electrophoresis together with 1 kb ladder (DNA size marker).

(3-4) Extraction by Phenol:Chloroform:Isoamyl Alcohol

The remains of the double-digestion solution (25 μl), 70 μL of 1× TE Buffer (pH8.0) and 100 μl of PCI solution were added into the centrifuge tube, and the tube was mixed by using a vortex. Then, the tube was centrifuged by using a micro centrifuge at 4° C. with 14,000 rpm for 5 minutes. Then, the aqueous layer was transferred to 1.5 ml of clean centrifuge tube. Hereto, 400 μL at of 95% ethanol, 25 μL of 10 M ammonium acetate, and 1 μL glycogen (20 mg/ml) were added, and then mixed sufficiently by using the vortex.

Next, it was centrifuged at 4° C. with 14,000 rpm for 5 minutes. Then, the supernatant was removed by aspiration to obtain a pellet. 300 μL of 70% ethanol was added on the pellet, it was centrifuged for 2 minutes with 14,000 rpm. The supernatant was carefully aspirated to remove, the pellet was air dried about for 15 minutes at room temperature.

After the pellet was dried, it was dissolved in 10 μL of sterilized 1× TE Buffer (pH 8.0), and the solution was stored at −20° C.

(4) Construction of the Recombinant Adeno-X Plasmid DNA (4-1) Subcloning of the Expression Cassette into Adeno-X Virus Genome The reagents shown in the following table 2 were added into the 1.5 ml of the sterilized micro centrifuge tube in order. Then, it was mildly mixed and lightly centrifuged. After that, it was incubated at 16° C. for overnight.

TABLE 2

| Reagent and others | Liquid vulume (μL) |
|---|---|
| PI-Sce I/I-Ceu I digested pShuttle2 plasmid DNA | 2.0 |
| PI-Sce I/I-Ceu I digested pShuttle2-lac Z plasmid DNA | — |
| sterilized water | 3.0 |
| 10× DNA Ligation Buffer | 1.0 |
| Adeno-X Viral DNA(250 ng/μl) | 3.0 |
| DNA Ligase(1 unit/μL) | 1.0 |
| Total | 10.0 |

90 μL of 1× TE Buffer (pH 8.0) and 100 μL of PCI solution were added to each sample, and then it was mildly mixed by using vortex. It was centrifuged at 4° C. with 14,000 rpm for 5 minutes, and the aqueous layer was transferred to 1.5 mL of the clean micro centrifuge tube. Then, 400 μL of 95% ethanol, 25 μL of 10M ammonium acetate solution, and 1 μL of glycogen (20 mg/ml) were added to the tube, and then it was mildly mixed by using the vortex.

It was subjected to the centrifugation at 4° C. for 5 minutes with 14,000 rpm, and the supernatant was removed by the aspiration to obtain the pellet. The following ethanol precipitation operations were the same as those of (3-4).

After the pellet was dried, it was dissolved in 15 μL of the sterilezed deionized water.

(4-2) Swa I Digestion of the Recombinant Adeno-X Plasmid DNA

The digestion solution as shown in the following table 3 was prepared, and added into each sample in the centrifuge tube. Then, they were incubated for 2 hours at 25° C.

TABLE 3

| Reagent and others | liquid volume (μL) |
| --- | --- |
| ligation product | 15 |
| 10× Swa I Digestion Buffer | 2.0 |
| 10× BSA | 2.0 |
| Swa I (10 units/μL) | 1.0 |
| Total | 20.0 |

80 μL of 1× TE Buffer (pH8.0) and 100 μL of PCI solution were added to each sample, and then it was mildly mixed by using the vortex. It was centrifuged with micro centrifuge tube at 4° C. for 5 min with 14,000 rpmThe following ethanol precipitation operations were the same as those of (3-4), and the dissolved solution of the pellet was stored at −20° C. until use.

(4-3) Confirmation of the *E. coli* Transformant by the Recombinant Adeno-X Plasmid DNA The electroporation competent cell (*E. coli*) was transformed with the Swa I digested products obtained in (4-2) by using Supercharge EZ10 Electrocompetent Cell (the product code 636756).

The transformant mixture was plated on the agar plate, which is the mixture of LB medium and ampicillin (final conc. 100 μg/mL) (herein after, it is referred to as "LB/Amp agar plate".), and then they are incubated at 37° C. for overnight to select ampicillin resistant (Ampr) transfomant. About $10^6$ cells of the colonies were obtained. The obtained colonies were checked by using Adeno-X System PCR Screening Primer Set attached to the product. The bacterial cells obtained from the single colony were plated in 5 mL of fresh LB/Amp liquid medium, and incubated overnight. The next day, according to the mini-scale method as mentioned below, Adeno-X plasmid DNA was purified.

(4-4) Mini-scale Preparation of the Recombinant Adeno-X Plasmid DNA 5 mL of log phase culture medium was centrifuged with 14,000 rpm for 30 seconds to remove the supernatant. The pellet was centrifuged with 10,000 rpm for 1 minute again, and then the supernatant was removed by using the micropipette.

Hereto, 150 μL of the buffer 1 was added and mildly pipetted to resuspend. 150 μL of the buffer 2 was added into the cell suspension. Then the cell suspension were mildly inverted to mix and stood for 5 minutes on ice. 150 μL of the buffer 3 was added to the cooled cell suspension, and then it was inverted to mix again and stood for 5 minutes on ice.

The cell suspension was centrifuged at 4° C. with 14,000 rpm for 5 minutes, and the transparent supernatant was transferred into 1.5 ml of the clean centrifuge tube. 450 μL of PCI solution was added to the supernatant, and then inverted to mix. Then, it was centrifuged at 4° C. with 14,000 rpm for 5 minutes, and the aqueous layer was transferred to the clean 1.5 ml of the micro centrifuge tube.

The following ethanol precipitation operations were the same as those of (3-4), and the dissolved solution of the pellet was stored at −20° C. until use. The rDNA of the interest was identified by using the analysis with the restriction enzymes and PCR as described below.

(5) Restriction Site Analysis of the Obtained rAdeno-X Plasmid DNA

Analysis was performed by using PI-Sce I and I-Ceu I. The reagents shown in the following table 4 was entered into 1.5 ml of the micro sterilized centrifuge tube. Then, 30 μL of PI-Sce I/I-Ceu I double digestion solution was added to it, and then sufficiently mixed and then it was lightly rotated to collect the contents.

TABLE 4

| Reagent and others | liquid volume (μL) |
| --- | --- |
| sterilized water | 19.5 |
| 10× double-digention solution | 3.0 |
| rpAdeno-X DNA (500 ng/μl)(500 ng/μl) | 2.0 |
| pShuttle2-lac Z plasmid (500 ng/μl) | — |
| PI-Sce I (1 unit/μl) | 2.0 |
| I-Ceu I (5 unit/μl) | 0.5 |
| 10× BSA | 3.0 |
| total | 30.0 |

It was incubated at 37° C. for 3 hours to perform restriction treatment. The reaction mixture after the treatment was subjected to 1% agarose/EtBr gel electrophoresis to obtain the culture medium.

(6) Production of the Recombinant Adenovirus (6-1) Preparation of the rAdeno-X Plasmid DNA for HEK293 Cell Transfection The reagents shown in the following table 5 was entered into the 1.5 ml of the sterilized centrifuge tube to be mixed, and then it was lightly centrifuged by using the micro centrifuge. Then, it was incubated at 37° C. for 2 hours to treat the rAdeno-X plasmid DNA with Pac I restriction enzyme.

TABLE 5

| Reagent and others | liquid volume (μL) |
| --- | --- |
| sterilized water | 20 |
| pAdeno-X plasmid DNA (500 ng/μl) | 10 |
| 10× Pac I Digestion Buffer | 4 |
| 10× BSA | 4 |
| Pac I (10 units/μL) | 2 |
| total | 40 |

60 μL of 1× TE Buffer (pH 8.0) and 100 μL of PCI solution were added to it, and then it was mildly mixed by using the vortex. Then, it was centrifuged by using the micro centrifuge at 4° C. for 5 minutes with 14,000 rpm. The aqueous layer was carefully transferred into 1.5 ml of the clean sterilized centrifuge tube.

The following ethanol precipitation operations were the same as those of (3-4), and the dissolved solution of the pellet was stored at −20° C. until use.

(6-2) Transfection of Pac I Digested Adeno-X Plasmid DNA into HEK293 Cell

Before 24 hours of the plasmid DNA transection, HEK 293 cells were plated on the 60 mm culture plate so as that the cell number was about 1 to $2\times10^6$ (about 100 cells/mm$^2$). Then, they were incubated at 37° C. in the presence of 5% $CO_2$.

10 µL of Pac I-digested Adeno-X plasmid DNA was transfected to each culture plate to introduce Adeno-X DNA into the HEK293 cell, according to a standard transfection method (CalPhos Mammalian Transfection Kit, the product code 631312). It was confirmed whether CPE (cytopathic effect) occurs or not from the next day of the transfection.

One week later, the cells adhered on the bottom or side wall of the culture plate was released by mild mixing. The obtained cell suspension was transferred into 15 mL of the sterilized centrifuge tube having a conical bottom, and it was centrifuged at room temperature for 5 minutes with 1,500×g.

The obtained precipitate was suspended in 500 µL of the sterilized PBS. The solution was subjected to the freeze-thaw operation for 3 times, which is frozen in dry ice/ethanol and thawed in the incubator with 37° C., to obtain the lysate in which the cells were sufficiently thawed. Next, it was lightly centrifuged to remove suspended matter, and then the supernatant was transferred into the sterilized another tube to use immediately. The lysate, which was not used immediately, was stored at −20° C.

250 µL of the lysate was added onto the cultured cells in the 60 mm plate, and continued to culture. Note that by using anti-Hexon antibody included in Adeno-X Rapid Titer Kit (the product code 631028), the titer of the adenovirus was measured according to the instruction manual (PT3651-1) of the kit.

(6-3) Virus Amplification for Preparing the Virus having High Titer

Before 24 hours of the titration assay, HEK293 cell were plated on a T75 flask, and they were incubated at 37° C. in the presence of 5% $CO_2$ overnight to be confirmed that they became 50 to 70% of confluent.

Next day, the medium was exchanged the new one including the virus to infect them with the virus at MOI=10. After the incubation at 37° C. in the presence of 5% $CO_2$ for 90 minutes, the flask was taken out and 10 mL of the medium was added into the flask.

They were cultured at 37° C. for 3 to 4 days in the presence of 5% $CO_2$, and CPE was confirmed. After 50% of the cells were released, the released cell suspension was prepared as described above, then it was transferred to 15 mL of the sterilized centrifuged tube with the conical bottom. The freeze and thaw operation as described above was performed, and the cells were thawed. By using Adeno-X Rapid Titer Kit (the product code 631028), the titer, $10^7$ PFU/mL of titer was obtained.

Western blotting was performed to confirm whether the packaged adenovirus genome has copies of the specific transcription unit against the target gene as the functional form.

(7) Adenovirus Infection to the Target Cells
(7-1) Infection to the Target Cells Before 24 hours of the infection, $1×10^6$ cells of SHED were plated on 6-well plate. Next day of the plating, the medium was removed, and 1.0 mL of the medium including virus was added to the center of each plate. The solution was spread evenly on a monolayer formed by the SHED.

It was incubated at 37° C. for 4 hours in the presence of 5% $CO_2$, and the virus was infected to SHED. Next, the fresh medium was added, and then incubated at 37° C. in the presence of 5% $CO_2$. From 24 to 48 hours after the infection, the expression of the introduced gene was analyzed time dependently.

(7-2) Analysis of the β-Galactosidase Expression of the Infected Cells

The β-galactosidase expression in the adherent cell infected with the Adeno-X-lacZ was assayed by using Luminescent β-gal Detection Kit II (the product code 631712, Clontec Laboratories Inc.).

Example 2

Manufacturing of SHED (1) Isolation of Dens Deciduous Stem Cell

An exfoliated dens deciduous obtained from 10 years old healthy boy were used. After the exfoliated dens deciduous was disinfected with Isodine solution, a crown of the teeth was horizontally cut by using the dental diamond point, and then the dental pulp tissue was collected by using the dental reamer. The obtained dental pulp tissue was digested in the solution including 3 mg/mL of type I collagenase and 4 mg/mL of disperse at 37° C. for 1 hour. Next, the solution was filtrated by using 70 mm of cell strainer (Falcon Inc.).

The filtrated cells were resuspended in 4 mL of the medium to be plated into the culture dish for adherent cell having the 6 cm in diameter. DMEM (Dulbecco's Modified Eagle's Medium) including 10% FCS was added into the dish and cultured for about 2 weeks in the incubator (desk top cell culture device for personal use, 9000EX series, Wakenbtech Co., LTD.) adjusted as 5% $CO_2$, at 37° C. The adherent cells formed colonies (the dental pulp stem cells) were treated by using 0.05% trypsin/EDTA for 5 minutes at 37° C., and then the cells released from the dish were collected.

Next, the adherent cells selected as mentioned above were plated on the culture dish for the adherent cells (a collagen coat dish), and they were incubated as primary culture in the incubator adjusted as 5% $CO_2$ at 37° C. to obtain the primary cultured cell. When the cells became macroscopically sub-confluent (about 70% of the surface of the culture container was covered by the cells), or confluent, the cells were treated by using 0.05% trypsin/EDTA at 37° C. for 5 minutes to be released from the container, and then collected.

Thus obtained cells were again plated on the dish including the medium, and perform passage in several times to be grown up to about $1×10^7$ cells/mL. The obtained cells were stored in the liquid nitrogen.

After that, by using the primary cultured cells, the passage was performed with the medium at the cell concentration of $1×10^4$ cells/cm$^2$. In the experiment, the cells passed from 1 to 3 were used. The human BMMSC (the bone marrow mesenchymal stem cell, Bone Marrow Mesenchymal stem cells) was purchased from Lonza Group Ltd. and cultured according to the manufacturer's instruction manual.

As described above, the human exfoliated dens deciduous dental pulp stem cells (SHED) were obtained. Among the obtained SHED, about $1×10^6$ cells of STRO-1 positive cells were sorted as follows from each sample by using FAC-STARPLUS (Becton, Dickinson and Company).

According to the manufacturer's instruction manual of the bromodeoxyuridine BrdU staining kit (Invitrogen), BrdU was incorporated into the cells for 12 hours to evaluate the growth rate of SHED (n=3 in each group). The experiments were repeated for 5 times. After one-way analysis of variance, Tukey-Kramer test was performed to evaluate statistical significant difference.

In order to detect STRO-1 with immunofluorescence, SHED was fixed with 3% paraformaldehyde, rinsed twice with PBS and then treated with 100 mM of glycine for 20 minutes. Next, these cells were permeabilized with 0.2% Triton-X (Sigma-Aldrich) for 30 minutes. Then, they were incubated in the mixture of 5% donkey serum and 0.5% bovine serum albumin for 20 minutes.

Next, the cells were incubated with the primary antibody, mouse anti-human STRO-1 antibody (1:100, R&D Inc.) for 1 hour, then incubated with the secondary antibody, goat anti-mouse immunoglobulin M-FITC antibody (1:500, Southern Biotech Corp.) for 30 minutes, and then mounted by using Vector Shield DAPI (Vector Laboratories Inc.).

After that, a-MEM supplemented with 15% FBS was added to the 6 well plate, and then the sorted cells were plated in each well for preparing clones. About 300 colonies among the proliferated cells were pooled for the test.

(2) Transgenesis

As described above, 4 genes, bmi-1, E6, E7 and hTERT were integrated into the adenovirus vector to manufacture a virus vector to express the gene products. As a reference, the control vector not integrated the genes was manufactured.

SHED was plated on the collagen coat dish having 100 mm$\phi$ of the diameter at the concentration of $1 \times 10^6$ cells, and then DMEM supplemented with 10% FBS was added. They were cultured until sub-confluent. The medium was removed by aspiration, and 500 μL of the virus solution diluted with the medium was added (MOI=10), and then incubated at 37° C. for 1 hour in the 5% $CO_2$ incubator for the virus vector infection. After 48 hours from the infection, the infected cells were incubated for 10 days in the medium supplemented with puromycin (1 pg/mL) to select. Then 500 to 600 of the resistant clones were pooled. Every 3 to 4 days, about $0.5 \times 10^5$ cells of SHED was plated to the culture dish having 100 mm$\phi$ of the diameter to perform passage. SHED to which the genes were transferred was named SHED-T, and SHED to which the genes were not transferred was named SHED-C.

Example 3

Figure 1:
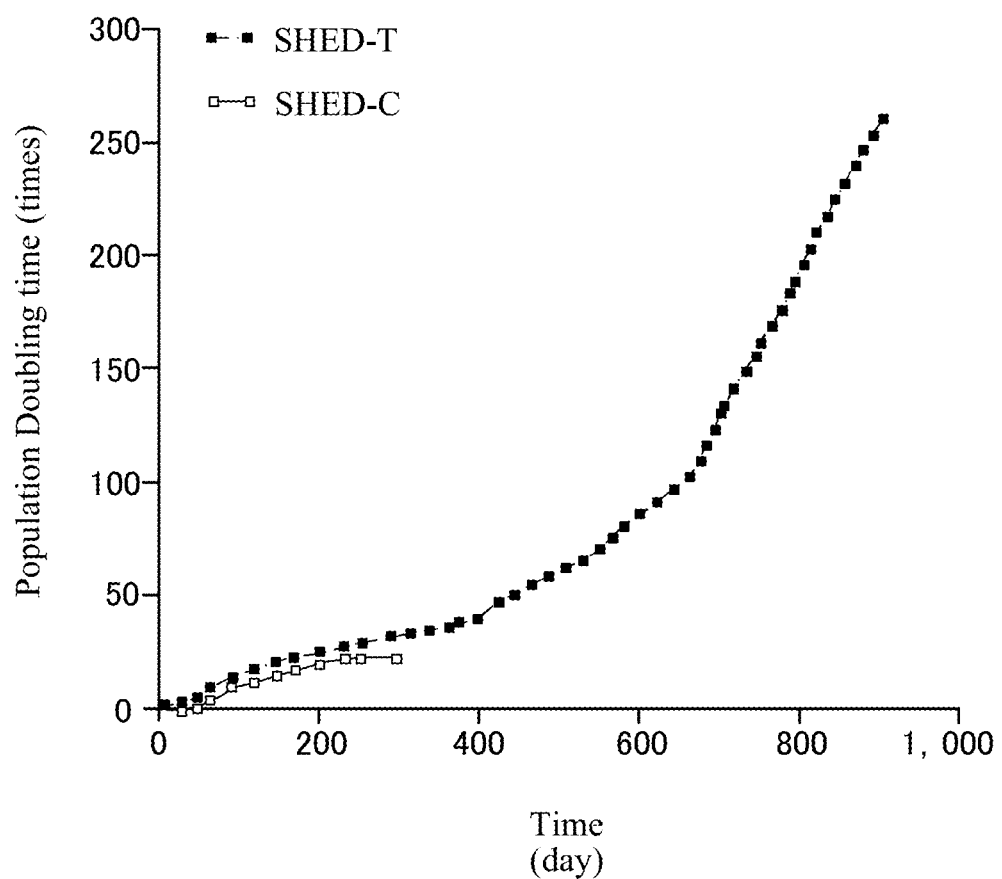
FIG. 1 is a graph showing a relationship between culturing times and population doubling times of the immortalized stem cell and non-immortalized stem cell.

Study of Feature of SHED (1) Measurement of the Growth Rates of SHED-C and SHED-T Status of the population doubling time of SHED-T (the gene transferred SHED) was shown in FIG. 1. In the figure, a vertical axis shows the population doubling time number (cell division number, times), and an abscissa axis shows the time period (date of culture). The status that SHED in culture did not divide for 1 month was as an evaluation standard of the aging.

The proliferation of SHED-C has stopped at about 30 times to enter aging or proliferation termination phase. In contrast, SHED-T passed over 250PD and proliferated after 800 days have passed.

(2) Flow Cytometry Analysis

Figure 2:
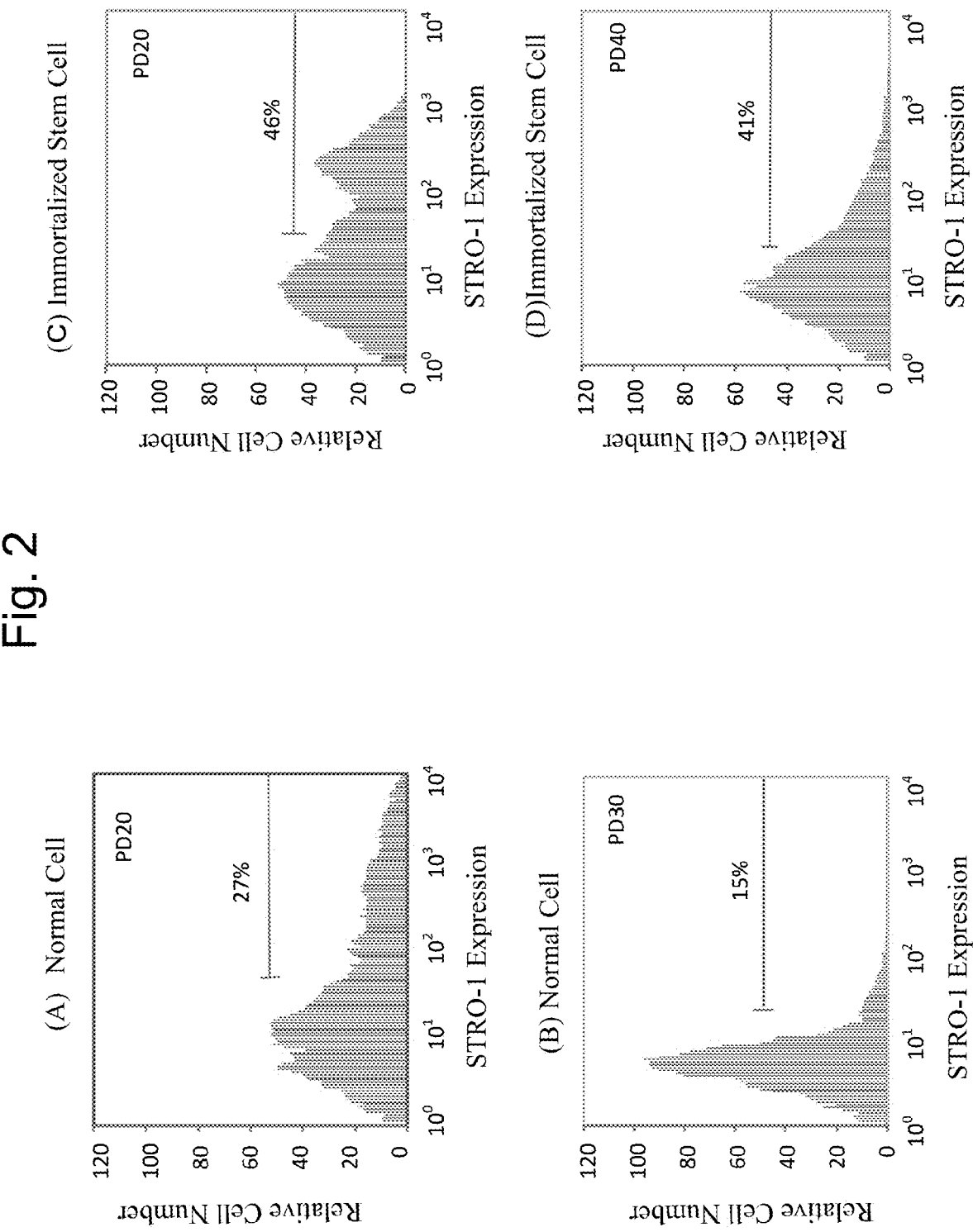
FIGS. 2(A), 2(B), 2(C), and 2(D) are graphs showing the results of STRO-1 expression in both SHED-C and SHED-T. In the figures, PD20 means that the population doubling number is 20, PD30 means that it is 30, and PD40 means that it is 40.

In order to obtain a suspension containing a single cell, the adherent monolayer cells were digested with trypsin/EDTA. The anti-STRO-1 monoclonal antibody (1:100) was added to $2 \times 10^5$ cells and stood to analyze by using FACS Calibur flow cytometer (Becton, Dickinson and company). When the fluorescence level of them was higher at the rate of more than 99% compared to the control antibody with corresponding to the same isotype, the expression was assessed to be positive. In both of SHED-T and SHED-C, the primary and later passage cells were fixed, and stained with FITC binding STRO-1 antibody. Then, it was analyzed by using the flow cytometry. The lest was repeated twice respectively. In SHED-C, the ratio of the STRO-1 positive cells was 27% at PD20, and decreased to 15% at PD30 (FIGS. 2(A) and (B)). The ratio of the STRO-1 positive cells in SHED T was 46% at PD20 and 41% at PD40, respectively (FIGS. 2(C) and (D)).

(3) Study for the Differentiation Ability

The differentiation abilities of SHED-C and SHED-T at PD0, PD10 and PD20 were studied by the forming ability of the newly generated bone mass and histological stain of the tissue.

Firstly, $2.0 \times 10^6$ cells of SHED-C or SHED-T were mixed with 40 mg of ceramic powder of hydroxyapatite/tricalcium phosphate (HA/TCP) (Olympus Corporation), and then the mixture was inoculated subcutaneously under a dorsal surface of immunocompromised mouse at 10 weeks old (NIH-bgnu-xid, female, Harlan Sprague Dawley Inc.).

Eight weeks after the inoculation, the inoculant was recovered, and fixed with 4% formalin to decalcify. Then, it was buffered by using PBS solution including 10% EDTA for paraffin embedding. A part of it was stored in 70% ethanol for embedding in resin.

Figure 3:
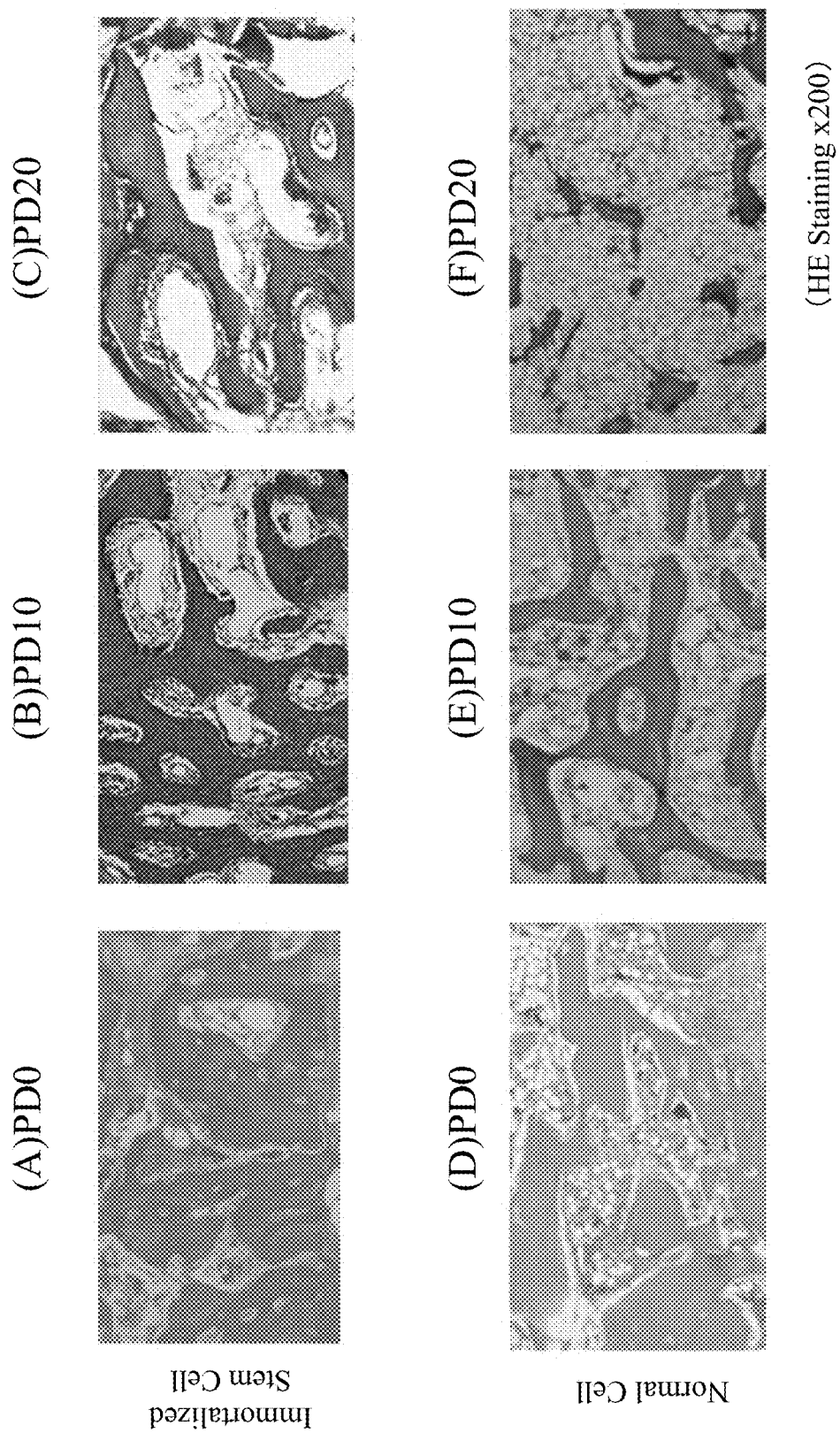
FIGS. 3(A), 3(B), 3(C), 3(D), 3(E), and 3(F) show the differentiation abilities of SHED-C and SHED-T at PD0, PD10 and PD20 by studying forming ability of the neonatal bone mass and histological staining of the tissue. $2.0 \times 10^6$ cells of SHED-C or SHED-T were mixed with ceramic powder of HA/TCP, and then the mixture was inoculated subcutaneously under a dorsal surface of the immunocompromised mouse at 10 weeks old.

A paraffin section was deparaffinized, and hydrated. After that, the section was stained with hematoxylin and eosin (herein below, it is referred to as "H&E".). FIGS. 3(A) to (C) show the stained images of SHED-T (the immortalized stem cell) at PD0 to PD20, and FIGS. 3(D) to (F) show the stained images of SHED-C (the normal cell) at PD0 to PD20. In order to quantify of the new born formation in vivo, the specified positions were chosen, and the area of the new born and the sight area were calculated to obtain the newly generated born mass from these values for the inoculant formed after SHED-T inoculation or SHED-C inoculation respectively.

Newly generated born mass=Newly generated born area/sight area×100

Figure 4:
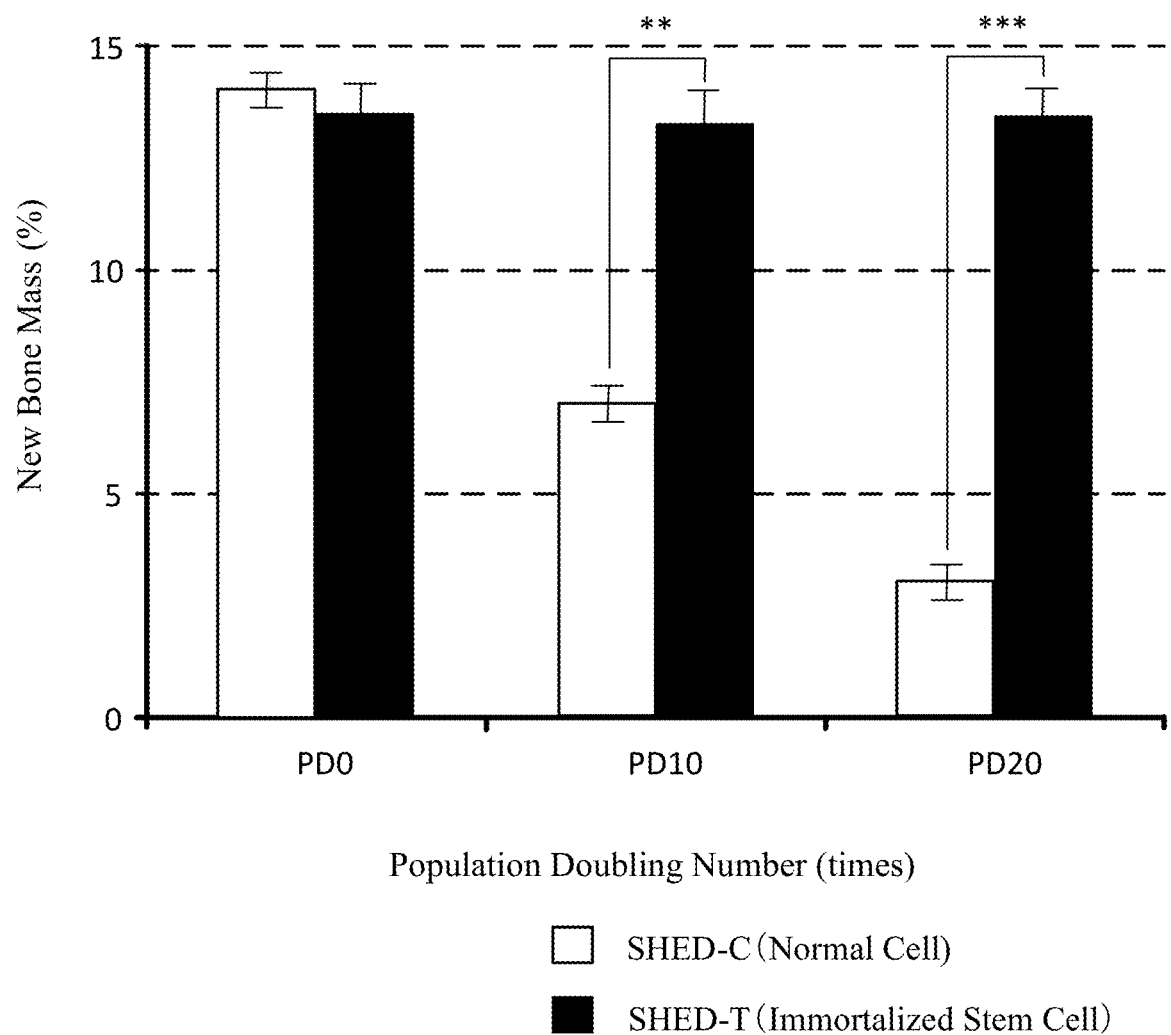
FIG. 4 is the graph showing the relationship between the population doubling time (number of times) and mass of newly generated bone. In the figure,  shows p <0.05, * shows p <0.01. The mass of newly generated bone are calculated by using the following equation.

FIG. 4 shows the change of the newly generated born mass of SHED-T and SHED-C at each population doubling number (doubling time). In the figure,  shows p<0.05, * shows p<0.01. Note that the newly generated born mass was obtained by using the following equation.

As shown in FIG. 4, the newly generated bone mass was decreased depending on the increase of the population doubling time in SHED-C, and it was decreased to about ⅕ at PD20 compared to that of PD0. In contrast, the bone generated bone mass was not changed till PD20 in SHED-T, and the bone mass in SHED-T showed 5 times higher than that of SHED-C at PD20.

(4) Evaluation of Canceration Activity $1 \times 10^6$ cells of SHED-C cells or SHED-T cells were inoculated to the subcutaneous tissue of the immune compromised mice. After inoculation, we observed more than 30 days. However, the tumor was not formed during the observation term in any mice to which the cells were inoculated. Also, all of the clones from the cultured cells between 40 to 200PD did not show any morphological change in SHED-T cells.

From the above, it was demonstrated that SHED-T had no canceration activity.

(5) Evaluation

It was demonstrated that SHED-T had proliferation ability, holding differentiation ability even after 260 PD. However, SHED-C had the differentiation ability, but aged not more than 30 PD.

As described above, it was demonstrated that SHED-T became the immortalized stem cell, and was suitable for large scale production of SHED supernatant having higher activity.

Example 4

Preparation of Conditioned Medium

The immortalized SHED prepared in example 1 was cultured in the serum free medium for 48 hours under the following condition of oxygen concentration of 20%, 10%, 5% and 1% respectively. Then, the supernatants were collected.

The production amount of cytokine shown in the following table 6 was measured by using ELISA kit (Catalog No.: DB100), Human TGF-β Quantikine Elisa kit (Catalog No.: DB100B) and Human VEGF Quantikine Elisa kit (Catalog No.: DVE00)

TABLE 6

| Group | Oxygen concentration (%) | Production amount of cytokine (pg/mL) | | | |
|---|---|---|---|---|---|
| | | IGF-1 | VEGF | TGF-β1 | SDF-1 |
| I | 20 | 1,400 | 500 | 350 | 15 |
| II | 10 | 1,800 | 550 | 500 | 17 |
| III | 5 | 1,900 | 600 | 600 | 30 |
| IV | 1 | 2,100 | 800 | 1,770 | 45 |

As shown in FIG. 6, the production amounts of IGF-1, VEGF, TGF-β and SDF-1 were significantly high under the condition of low oxygen concentration. It shows that the production amounts of at least four types of cytokines were significantly increased by culturing under the condition of low oxygen concentration.

Example 5

Study of Therapeutic Effect by Using Tumor Bearing Animal

Mouse squamous cell cancer strain SCCVII (provided from Mr. Nishimura in medical school of Kinki University) was cultured in DMEM including 10% of FBS (Gibco Co.) at 37° C. for 1 week. Then, it was dispersed with PBS buffer including 0.5% trypsin. The number of viable cells stained by trypan blue was counted. Then, 1×10$^6$ cell/ml of the suspension was prepared with 1 mL of PBS buffer.

0.5 ml of the cell suspension (5×10$^5$ cells/mouse) as prepared as described above are subcutaneously administrated into the back of 50 mice (C3H/He, 7 week-old, purchased from Chubu Kagaku Shizai Co., LTD.) by using 18G injection needle (product by Terumo Co.). Each group has 10 mice.

1 ml of culture supernatant of control group (buffer only) and those of group I to group IV (hereinafter, they are sometimes referred to as "G I to G IV") were administered to each group of mice via tail vein.

After the cancer cell injection, each group of mice was bred respectively on the same condition as described above.

Each group of mice was put in the cage to breed under the condition of light-dark cycle of 12 hours at 25±0.5° C. in 50% humidity. Water and feed were freely fed. The diameter of the tumor was measured by using calipers every day.

When the diameter of the tumor in the mouse, which was formed by SCCVII injection, was over 6 mm, 1 ml of each culture supernatant of GI to GVI cultured under the different oxygen concentrations was injected into each mouse via tail vein as one shot. The increased tumor diameter of each group was shown in FIG. 5.

In GI, the tumor diameter exceeded 10 mm at the 3$^{rd}$ day after dosing of the culture supernatant, and 20 mm at 14$^{th}$ day after dosing of them. The increase rates of the tumor diameter both of GII and GIII were significantly slow than that of GI (*shows p<0.05). The diameter exceeded 10 mm at the 7$^{th}$ day after dosing of them, and 20 mm at the 9$^{th}$ day after dosing of them.

In contrast, the increase of the tumor diameter in GIV was significantly slow (**shows p<0.01), and the average did not exceeded 10 mm even at 21$^{st}$ day after dosing of them. Furthermore, since tumor regression was observed after 14$^{th}$ day of dosing them, the standard deviation became larger. FIG. 6 shows the photographs of the mouse; FIG. 6(A) shows at the status of diameter was maximum, and FIG. 6(B) shown complete healing.

The mice viability transitions of each group of the mice were shown in FIG. 7. The differences of growth rates of tumor diameters reflected in the mice viability. All of the mice died at 41$^{st}$ day in GI. Also, all of the mice died at 50 day in GII and GIII. In contrast, about 80% of the mice were alive even if 60 days passed in GIV, and i all of the mice died at 78$^{th}$ day. The lifetime of the mice in GIV was about double as that of GI.

Example 6

Study Related to the Change of Tumor and Surrounding Tissue Thereof

The behavior of macrophage to tumor tissue was measured by using in vivo imaging. Five ml of thioglycolate solution (2% of Brewer's thioglycolate medium (Difco Co.) was injected into each mouse intraperitoneally. Four days later of the injection, the peritoneal lavage was conducted with PBS, and 10$^7$ cells of macrophage were obtained. 3×10$^6$ cells in the obtained macrophages were mixed with 5 μg/ml of pigment (MolecularTracer Dir (Summit Pharmaceutical International Co.)) and 0.5% of ethanol to be labelled.

The culture supernatant prepared in example 2 was injected into each group of the mice via tail vein at 1 mL/mouse. The amount of cytokine in the culture supernatant was measured by using Human IGF-1 Quantikine Elisa kit, Human TGF-β Quantikine Elisa kit, Human VEGF Quantikine Elisa kit as described above. The behavior of the labeled macrophage was observed by using Xenogen IVIS 200 series system (Xenogen, Alameda, Calif.). The recommended IVIS filter (excitation of 710 nm/fluorescence of 760 nm) was used in the imaging, which was performed at 748 nm of excitation wavelength and 780 nm of fluorescence wavelength.

The labeled macrophage labelled began to move within an hour in GIV. Then, it was accumulated as surrounding the entire tumor (FIG. 8). Invasive image of the macrophage was seen at the groin of right rear leg in which tumor has been formed in the figure. Such accumulation of the macrophage around the tumor was not observed in GI to GIII.

Example 7

Histological Study

5×10$^5$ cells of SCCVII were injected into CH3/He mice. Then, the tumors with peripheral tissue were removed from the mice both after 1 and 15 week of the injection. Then, these tissues were subjected to histological autopsy. An example recognized as tumor necrosis was seen in the treated group (GIV) at 15 week (FIG. 6).

Also, CD11b antibody was used as a macrophage maker, CD206 antibody was used as M2 macrophage maker, and ED1 (CD68) was used as macrophage maker respectively to stain. Then, the ratio of M1 to M2, which were subpopulations of macrophage, was studied. The result was shown in FIG. 9.

As shown in FIG. 9, the ratio of M2 was larger (Ml dominant) at the early stage of tumor generation (1 week after cell injection). In contrast, the ratio of M1 and M2 was reversed (M1 dominant) at the later stage (15 week after cell injection). When the tumor tissue was investigated by Western blotting, it showed that TGF-β inhibitor (Trabedersen, LAP 12009) and the like was expressed largely in M1 in contrast with that TGF-β-super family was expressed largely in M2.

Figure 10:
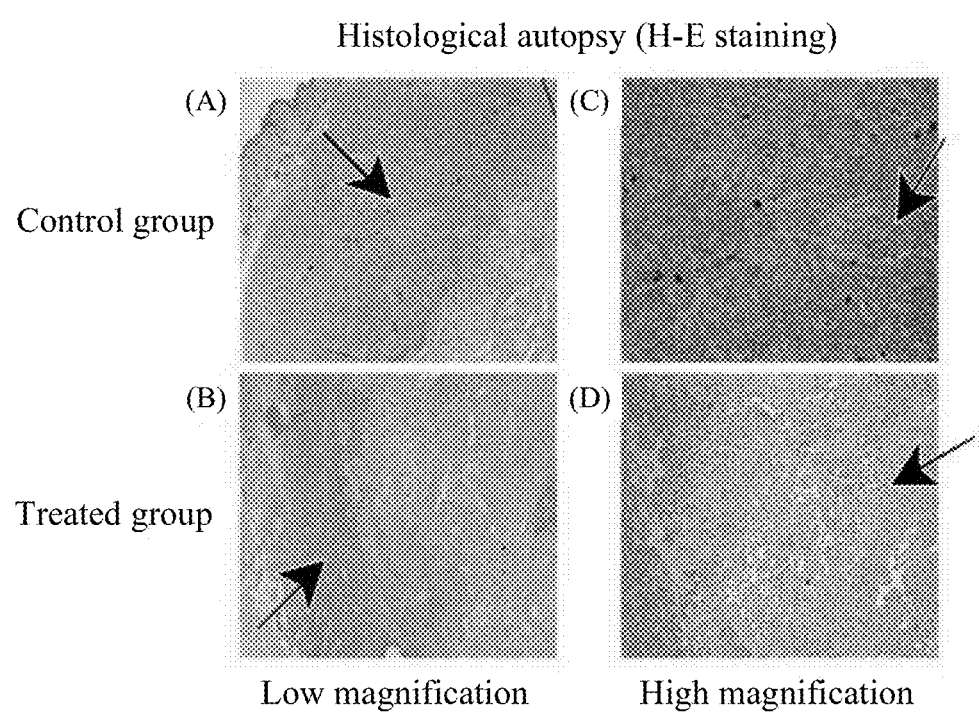

The staining images of the tumor tissues of the mice by eosin-hematoxylin staining of control group and treated group were shown in FIG. 10. When staining images of the control group (A) and treated group (B) with low magnification rate was compared, it shows that slightly dead region was included in the tumor tissue in the staining image of treated group. When magnification rate was increased, the difference was clearly observed (FIGS. 10(C) and (D)).

From the above, it was shown that the dental pulp stem cell responses to the hypoxic condition to increase and activate the specific cytokine related to the tumor growth. And, as a result, migration ability of macrophage was increased and accumulated highly in the tumor tissue.

Furthermore, it was shown that the macrophage accumulated in the tumor destroys the tumor tissue with native phagocytosis ability and at the same time inhibits tumor growth through the TGF-β.

INDUSTRIAL APPLICABILITY

The present invention is useful to the pharmaceutical field.

The invention claimed is:

1. A method of making conditioned medium, the method comprising:
   (a) transfecting dens deciduous dental pulp stem cells with nucleic acid sequences encoding hTERT, bmi-1, E6 and E7;
   (b) selecting an immortalized dens deciduous dental pulp stem cell or cells that has at least one of: (1) a 1.5 to 3 times higher expression ratio of STRO-1 positive cells as compared to non-transfected dens deciduous dental pulp stem cells at population doubling times 20 or 40, (2) a neonatal bone quantity production ability five times greater than that of a primary dens deciduous dental pulp stem cell at population doubling times of 20, or (3) combinations thereof;
   c) culturing immortalized dens deciduous dental pulp stem cells selected in step b) in serum free medium in 0.5% to 1% oxygen at 23-27° C.; and
   d) isolating conditioned medium from the immortalized dens deciduous dental pulp stem cells cultured in step c),
   wherein the conditioned medium comprises more than 1.5 times higher concentration of both insulin like growth factor 1 (IGF-1) and vascular endothelial cell growth factor (VEGF) as compared to conditioned medium prepared by culturing immortalized dens deciduous dental pulp stem cells selected in step b) in serum free medium in 20% oxygen at 23-27° C.

2. The method according to claim 1, wherein said culturing in step c) is for 40 to 56 hours.

3. The method according to claim 1, wherein the conditioned medium comprises at least 5 times higher concentration of transforming growth factor β1 (TGF-β1) as compared to conditioned medium prepared by culturing immortalized dens deciduous dental pulp stem cells selected in step b) in serum free medium in 20% oxygen at 23-27° C.

4. The method according to claim 1, wherein the conditioned medium comprises at least 3 times higher concentration of stromal cell-derived factor 1 (SDF-1) as compared to conditioned medium prepared by culturing immortalized dens deciduous dental pulp stem cells selected in step b) in serum free medium in 20% oxygen at 23-27° C.

* * * * *